United States Patent [19]

De Claviere

[11] Patent Number: 5,443,441
[45] Date of Patent: Aug. 22, 1995

[54] APPARATUS AND METHOD FOR TRANSDERMAL DELIVERY OF COSMETIC COMPOSITIONS

[76] Inventor: Anne Marie De Claviere, 92 Sunken Orchard La., Oyster Bay Cove, N.Y. 11771

[21] Appl. No.: 151,606
[22] Filed: Nov. 12, 1993

Related U.S. Application Data

[63] Continuation-in-part of Ser. No. 26,949, Mar. 5, 1993, abandoned.

[51] Int. Cl.⁶ .............................................. A61N 1/30
[52] U.S. Cl. ........................................ 604/20; 604/19
[58] Field of Search ................................... 604/19, 20

[56] References Cited

U.S. PATENT DOCUMENTS

| | | | |
|---|---|---|---|
| 4,878,892 | 11/1989 | Sibalis et al. | 604/20 |
| 4,957,480 | 9/1990 | Morenings | 604/20 |
| 5,006,108 | 4/1991 | La Prade | 604/20 |
| 5,169,384 | 12/1992 | Bosniak et al. | 604/20 |

Primary Examiner—C. Fred Rosenbaum
Assistant Examiner—N. Kent Gring
Attorney, Agent, or Firm—Cohen, Pontani, Lieberman, Pavane

[57] ABSTRACT

An apparatus for enhancing transdermal delivery of cosmetic compositions including an electrical power source for generating varying levels of AC and/or DC current. The power source is arranged to be in electrically cooperative relationship with a cosmetic composition applied to a person and includes at least one positive electrode, and one negative electrode, and further includes current varying means for varying the output of current from the power source in a range of about 0.1 mA to about 10 mA. A method for enhancing transdermal delivery of a cosmetic composition to the face of a person is also disclosed.

5 Claims, 2 Drawing Sheets

APPARATUS AND METHOD FOR TRANSDERMAL DELIVERY OF COSMETIC COMPOSITIONS

CROSS REFERENCE TO RELATED APPLICATION

This application is a continuation-in-part of commonly assigned, U.S. patent application Ser. No. 08/026,949, filed Mar. 5, 1993, abandoned.

BACKGROUND OF THE INVENTION

1. Field of the Invention

This invention relates to transdermal delivery of cosmetic compositions. More particularly, this invention relates to apparatus and methods which utilize electrical current to enhance the delivery of cosmetic composition into the skin of a person.

2. Background of the Invention

There exists a wide variety of cosmetic compositions for the beautification and/or therapeutic treatment of skin. Similarly, there are many different methods available for applying these cosmetic compositions to selected areas of the skin. Typically, the method of applying the cosmetic composition comprises merely manual smoothing of the cosmetic composition over the skin, then allowing the cosmetic composition to remain in place for a desired length of time. Exposing the applied cosmetic composition to heat and/or sunlight are additional procedures well known to effect beneficial therapeutic results. See, e.g., U.S. Pat. No. 4,885,157 wherein the use of sunlight, either artificial or natural, is directed onto the cosmetically treated skin for a period of 15 to 60 minutes. Another known cosmetic composition treatment procedure involves the massaging of the cosmetic composition into the skin. See, e.g. U.S. Pat. No. 4,849,211 wherein ache medication is lightly massaged into the skin. Cosmetic compositions are also known to be applied in several layers as described in U.S. Pat. No. 4,885,157 wherein a very thin layer is first massaged into the skin. A second and third layer are subsequently applied to complete the treatment which generally varies from 15 to about 60 minutes in length.

There exists a variety of electrical apparatus configured for physiotherapy and rehabilitation. Such apparatus include the BFA module, the USA module and the FMC module available from ETM of Paris, France. These apparatus utilize currents, for example, with intensity and frequency variation in order to increase therapeutic efficacy when treating muscle fibers. Other known electrical apparatus are configured for transdermal drug delivery. These drug delivery systems provide for electrically-assisted delivery of drugs, and also provide for enhanced drug transport at rates higher than those achieved by passive diffusion. This concept is based upon basic principles of electrochemistry and is defined as electrically-assisted transport, hereinafter referred to as "electrotransport". An electrochemical cell in its simplest form consists of two electrodes and associated half cell reactions, between which electrical current can flow. Electrical current flowing through the metal portion of the circuit is carried by electrons (electronic conduction), while current flowing through the liquid phase is carried by ions (ionic conduction). Current flows as an electrical charge is transferred to chemical species in solution by means of oxidation and reduction charge transfer reactions at the electrode surfaces.

Face masks are also known to be utilized for electrotherapeutic treatment as described in U.S. Pat. No. 3,971,387 wherein the face mask has a distributed set of electrically connected contact buttons. The contact buttons are adapted to be placed over dampened padding covering the face and to complete electrical circuits between the face and the contact buttons. The mask is provided with clearance openings for the eyes and nose to facilitate placement over the face of person. Low voltage current is applied to the face for various therapeutic purposes. In general, however, the various methods and apparatus used in connection with muscle therapy and drug delivery, including those which utilize face masks, have not been utilized in connection with cosmetic composition delivery.

The application of cosmetic compositions have heretofore not been totally satisfactory in beautifying and moisturizing the skin. The existence of methods and or apparatus which can more effectively apply cosmetic compositions so that the maximum beneficial effect can be realized, would be highly desirable. Accordingly, there is provided by the present invention an apparatus for transdermally delivering a cosmetic composition so as to maximize cosmetic benefits. Another object of the present invention is to provide a method for the application of cosmetic compositions in which cosmetic benefits are maximized.

These and other objects, as well as the scope, nature and utilization of the invention, will be apparent to those skilled in the art from the following description and the appended claims.

SUMMARY OF THE INVENTION

In accordance with the foregoing objectives, provided herewith is an apparatus for enhancing transdermal delivery of cosmetic compositions which comprises an electrical power source for generating varying levels of AC and/or DC current. The power source is arranged to be in electrically cooperative relationship with a cosmetic composition applied to a person. The power source comprises at least one positive electrode, and one negative electrode, and further comprises current varying means for varying the output of current from the power source in a range of from about 0.1 mA to about 10 mA. The apparatus further comprises means for connecting the positive electrodes to a portion of skin having cosmetic composition applied thereto and means for connecting the negative electrode to a portion of skin not having cosmetic composition applied thereto. In a preferred embodiment the power source further comprises waveform selection means for generating clipped and inverted AC signals. In another embodiment the apparatus is configured to operate on DC power.

In a preferred embodiment, a mask is provided which is configured to be placed on the face of a person and is preferably configured and dimensioned for holding the cosmetic composition therein. A permeable membrane portion may be used and is configured to lie between the cosmetic composition and the face of the person. The membrane is preferably permeable to the cosmetic composition when the cosmetic composition has an electric charge applied thereon which exceeds a specified threshold value. Means for connecting the positive electrode to the mask is provided so that the cosmetic composition therein is in electrical communication with the electrical power source. In another embodiment, the mask is electroconductive. Preferably, the mask is formed with a plurality of holes therethrough so that when the mask is placed on the face of a person, the holes will be positioned substantially over the nostrils, eyes and/or mouth of the person.

A method is disclosed for enhancing transdermal delivery of a cosmetic composition to the face of the person whereby the cosmetic composition is responsive, in terms of transdermal migration, to an electric field, comprising the steps of mixing together a cosmetic composition comprising 2-6 ml of a 2% elastine solution, 500-1000 mg collagen, 0.1-0.3 mg magnesium, 0.04-0.15 mg potassium, 0.07-0.2 mg manganese, 0.04-0.15 mg cobalt, and 75-125 ml water; and placing an absorbent material upon a portion of the skin to be treated, placing the cosmetic composition onto the absorbent material, and applying an electrical current in a range of 0 to 10 mA. to the person to enhance the transdermal penetration of the cosmetic composition into the skin.

In another preferred method, the cosmetic composition is placed within an electroconductive mask having a semipermeable membrane and an exterior portion. The mask is placed on the face of a person with the semipermeable membrane in contact with the face and an electrical current is applied in a range of about 0.1 mA to about 10 mA to the person for causing the migration of the cosmetic composition through the semipermeable membrane and transdermally into the face of the person.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
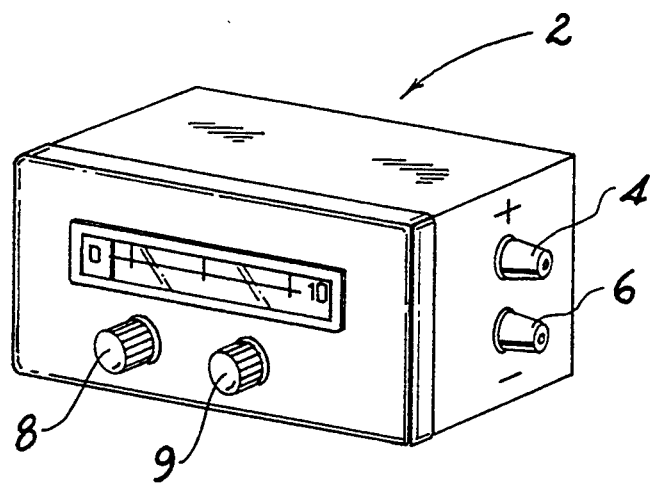
FIG. 1 is a perspective view of the electrical power source of the present invention.

Referring initially to FIG. 1, electrical power source 2 of the present invention includes a positive electrode 4, a negative electrode 6, current varying means 8 for varying of current from said electrical power source 2 in a range of from about 0.1 mA to about 10 mA and waveform selection means 9 for selecting the signal characteristics of the current.

Figure 2:
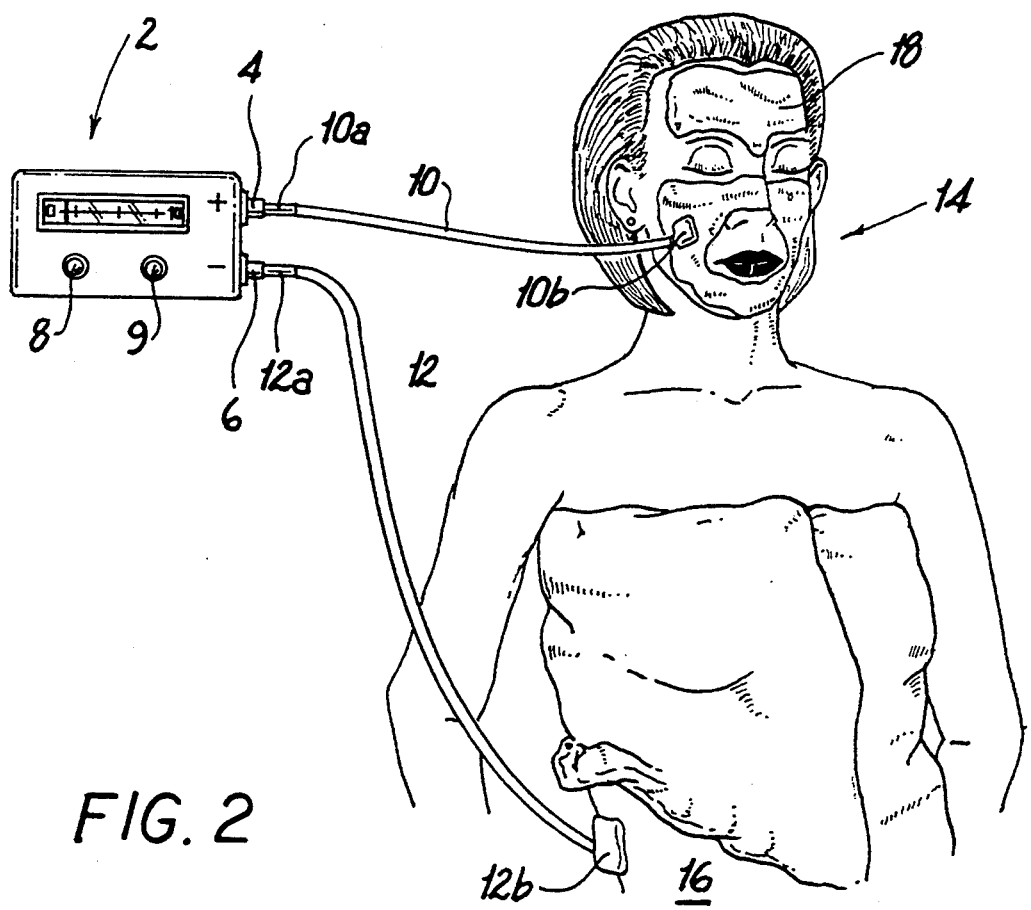
FIG. 2 is a frontal view according to an embodiment of the present invention wherein a cosmetic composition is being transdermally delivered to a skin portion of the person.

In a preferred embodiment of the present invention as shown in FIG. 2, positive electrode 4 is attached to a first end 10a of positive electrode connecting means 10. A second end 10b of positive electrode connecting means 10 is attached to the person at cosmetically treated facial skin portion 14. Negative electrode 6 is attached to a first end 12a of negative electrode connecting means 12. A second end 12b of negative electrode connecting means 12 is attached to the person at a non-cosmetically treated skin portion 16.

Referring to FIGS. 1-2, as electrical power supply 2 generates an electric potential, the electric potential is transferred out from positive electrode 4 and through positive electrode connecting means 10 to cosmetically treated facial skin portion 14. In response to the application of this electric potential, electrical current is generated and flows out of the person from non-cosmetically treated skin portion 16 through negative electrode connecting means 12 and into electrical power source 2 via negative electrode 6. Cosmetic composition 18 in reaction to the electric current, migrates transdermally into said cosmetically treated facial skin portion 14.

Figure 3:
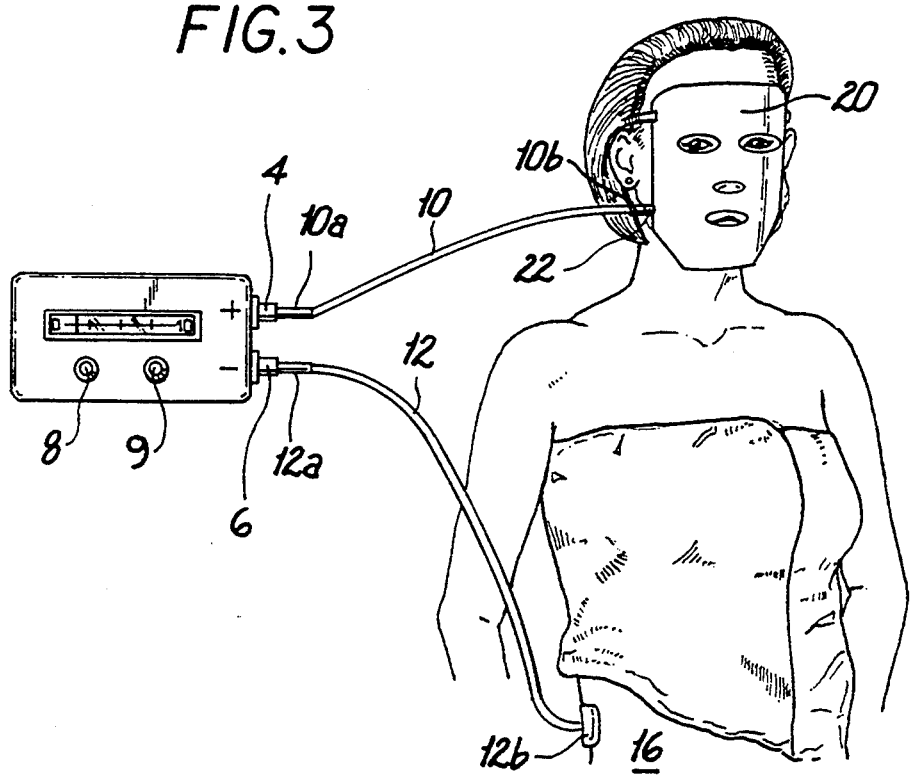
FIG. 3 is a frontal view according to a preferred embodiment illustrating a mask containing the cosmetic composition being transdermally delivered.
Figure 4:
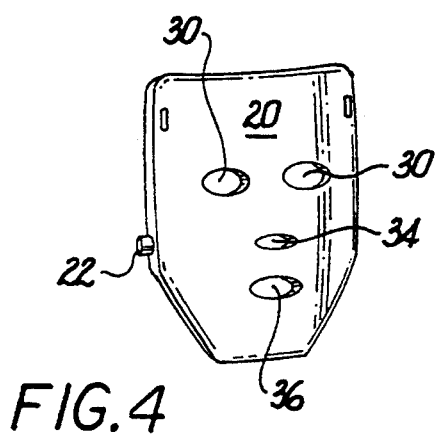
FIG. 4 is an enlarged view of the mask of FIG. 3.
Figure 5:
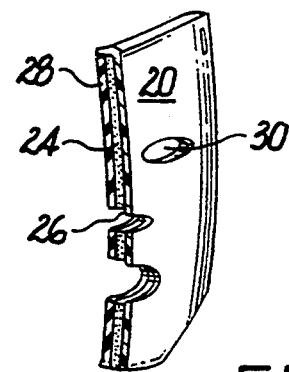
FIG. 5 is a cross-sectional view of the mask of FIG. 4 illustrating the selectively permeable membrane.

In the preferred embodiment of the present invention as shown in FIGS. 3-5, second end 10b of positive electrode connecting means 10 is attached to mask 20 at mask point 22. Mask 20 has a cavity 24 for receiving cosmetic composition 18 disposed between exterior portion 26 and semipermeable membrane 28. The semipermeable membrane 28 is configured to be permeable to the cosmetic composition 18 when the cosmetic composition 18 is exposed to electrical current. Mask 20 is configured to be placed on the face of a person with the semipermeable membrane 28 placed in contact with the face. Accordingly, mask 20 has formed therethrough eye holes 30, nose hole 32 and mouth hole 34 to permit the comfortable placement of mask 20 on the face of the person.

Referring once again to FIGS. 3-5, electrical power supply 2 generates an electric potential which is transmitted out from positive electrode 4, through positive electrode connecting means 10, to mask point 22 of mask 20. In response to the application of this electric potential and resulting electrical current, cosmetic composition 18 stored within storage portion 24 of the mask 20, migrates through semipermeable membrane 28 wherein the cosmetic composition 18 is transdermally delivered into the cosmetically treated facial skin portion 14.

Known apparatus used for stimulating muscle tissue are typically configured to generate current ranging generally up to 50 mA. Although these apparatus, for example the EMF BFA module which is configured to generate current up to about 25 mA, are usable as a power supply of the present invention, they possess higher than necessary capacities. As previously mentioned, the current required to transdermally deliver the cosmetic composition of the present invention is in the range of about 0.1 mA to about 10 mA. Accordingly, power supply 2 of the present invention is configured to generate current in a range of about 0.1 mA to about 10 mA.

Figure 6:
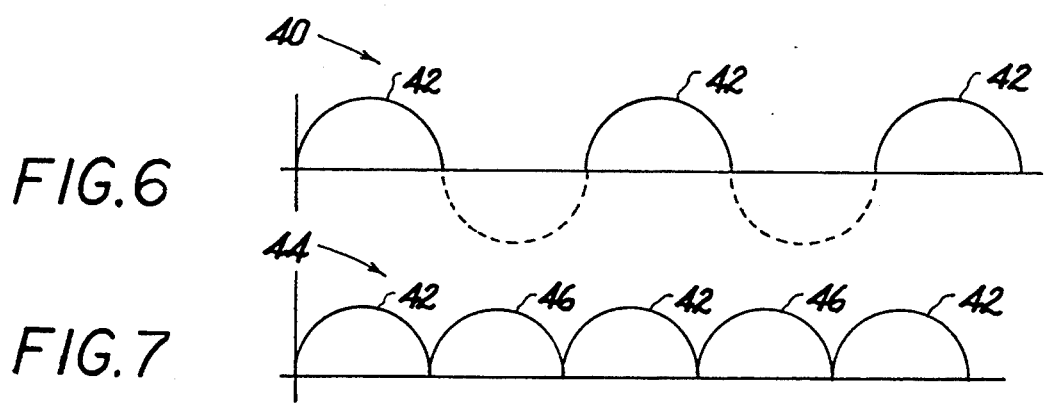
FIG. 6 is a graph of a clipped signal illustrative of the type of signals generated by the power source of a preferred embodiment of the present invention.
Figure 7:
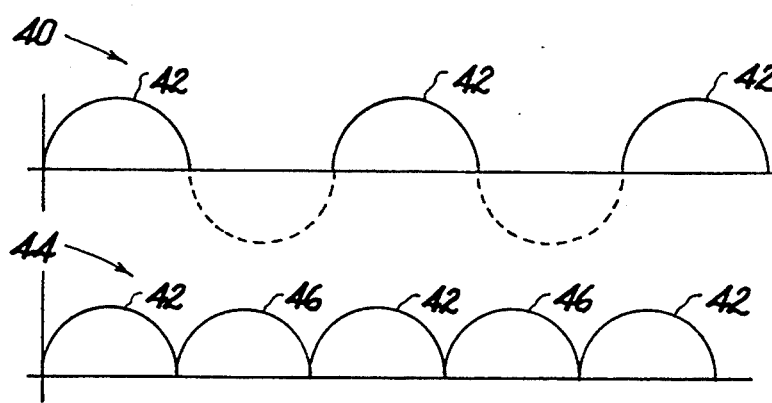
FIG. 7 is a graph view of an inverted signal illustrative of the type generated by the power source of a preferred embodiment of the present invention.

In a preferred embodiment of the present invention as shown in FIGS. 6-7, electrical power source 2 is configured to generate clipped signal 40 consisting of positive signal portions 42, and inverted signal 44 having alternating positive signal portions 42 and inverted negative signal portions 46. The clipped signal 40 and inverted signal 44 provide additional and effective electrical stimulus to the cosmetically treated skin portion.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An apparatus for transdermal delivery of cosmetic compositions, which comprises:
   (a) an electrical power source for generating a predetermined level of current, said power source comprising at least one positive electrode, and one negative electrode, said power source further comprising current varying means for varying the output of current from said power source in a range of about 0.1 mA to about 10 mA.;
   (b) a mask configured to be placed on the face of a person, said mask configured and dimensioned for receiving said cosmetic composition therein, said mask having a selectively permeable membrane portion disposed to lie between said cosmetic composition and the face of a person and wherein said mask is formed with a plurality of holes therethrough so that when said mask is placed on the face of a person, said holes will be positioned substantially over the nostrils, eyes and mouth of the person;
   (c) means for connecting said positive electrode to said mask so that said cosmetic composition in said mask is in electrical cooperation with said electrical power source; and
   (d) means for connecting said negative electrode to an area of skin not having a cosmetic composition applied thereto.

2. The apparatus according to claim 1, wherein the power source further comprises waveform selection means for generating clipped, and inverted AC signals.

3. The apparatus according to claim 1, wherein the apparatus is configured to operate on DC power.

4. The apparatus according to claim 1, wherein said selectively permeable membrane is permeable to said cosmetic composition when said cosmetic composition has an electric charge applied thereon which exceeds a specified threshold value.

5. The apparatus according to claim 1, wherein said mask is electroconductive.

* * * * *